United States Patent [19]

Houlihan

[11] 3,932,450

[45] Jan. 13, 1976

[54] INTERMEDIATES IN THE PREPARATION OF IMIDAZO(2,1-ALPHA)ISOINDOLES
[75] Inventor: William J. Houlihan, Mountain Lakes, N.J.
[73] Assignee: Sandoz, Inc., E. Hanover, N.J.
[22] Filed: Aug. 19, 1974
[21] Appl. No.: 498,273

[52] U.S. Cl.............................. 260/309.6; 260/999
[51] Int. Cl.²......................................... C07D 49/34
[58] Field of Search................................. 260/309.6

[56] References Cited
UNITED STATES PATENTS
3,657,269  4/1972  Houlihan ......................... 260/309.6

Primary Examiner—Ethel G. Love
Attorney, Agent, or Firm—Gerald D. Sharkin; Robert S. Honor

[57] ABSTRACT

Imidazo[2,1-a]isoindoles useful as anorexics and psychic-energizers are prepared from the N,o-dilithium derivative of substituted 2-phenyl-2-imidazoline by various routes.

4 Claims, No Drawings

INTERMEDIATES IN THE PREPARATION OF IMIDAZO(2,1-ALPHA)ISOINDOLES

This invention relates to a process for the preparation of imidazo[2,1-a]isoindoles of the formula

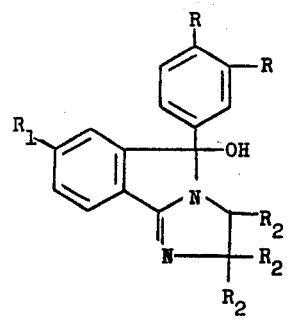

(I)

where
- each R independently, represents H, halo having an atomic weight of 19–36, methyl, or methoxy, or both R's together represent methylenedioxy, or one R at one time represents trifluoromethyl,
- $R_1$ represents H, halo as defined above, lower alkyl, i.e. alkyl having 1–4 carbon atoms, such as methyl, ethyl, isopropyl, and the like, lower alkoxy, i.e. alkoxy having 1–4 carbon atoms, such as methoxy, ethoxy, propoxy and the like, or trifluoromethyl, and
- each $R_2$ independently, represents H or alkyl having 1–2 carbon atoms, provided that
1. when $R_1$ is H, at least one of $R_2$ represents other than H,
2. no more than two of $R_2$ are other than H, and
3. when two $R_2$'s are alkyl, they are the same. These compounds are known to be useful as anorexiants and anti-depressants.

The compounds of formula (I) may also be represented by the tautomeric form (II)

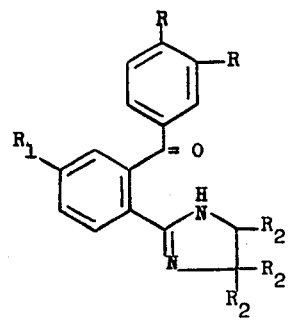

(II)

where
R, $R_1$ and $R_2$ are as above defined, this form being predominant in acid media whereas form (I) is predominant in basic media. To simplify this disclosure, however, only the compounds of formula (I) are to be discussed herein.

The compounds (I) may be prepared by treating the N,o-dilithiated derivative of a substituted 2-phenylimidazoline of the formula

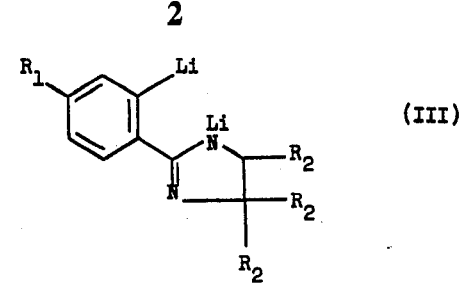

(III)

with a compound of the formula

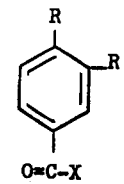

(IV)

where
- each R, $R_1$, $R_2$ and the provisos are as earlier defined, and
- X represents halo having an atomic weight of about 35–80, or $OR_3$, where $R_3$ represents straight chain loweralkyl, i.e., straight chain alkyl of 1–4 carbon atoms, such as methyl, ethyl and propyl, and hydrolyzing the resulting adduct.

This process is conducted by treating (III) with (IV) in inert atmosphere, such as nitrogen gas, and inert solvent such as a hydrocarbom, for example, hexane or heptane, or an ether, e.g., diethyl ether or tetrahydrofuran at a temperature of about 0°–100°C., preferably at about room temperature to the reflux temperature of the system, for about 0.5 to about 48 hours. The hydrolysis may be performed in conventional manner using, e.g. water, dilute mineral acid, ammonium chloride solution, and the like.

The compounds (I) are also preparable from the compounds of formula (III) by treating the latter with a nitrile of the formula

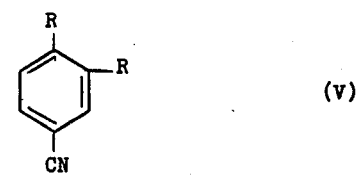

(V)

and hydrolyzing the resulting adduct to obtain a compound of formula (VI)

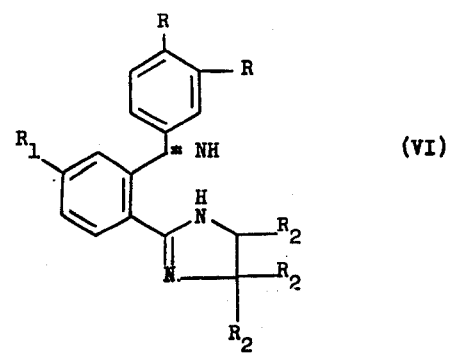

(VI)

where

R, $R_1$, $R_2$ and the provisos are as earlier defined, and treating (VI) (or an acid addition salt thereof) with water in the presence of acid. Accordingly, compounds (VI) may be prepared by treating (III) and (V) using the same reaction conditions, i.e., temperature, atmosphere, solvents and conventional hydrolysis, as earlier described with reference to the preparation of compounds (I) from compounds (III) and (IV). The compounds (VI) or a salt thereof are then treated with dilute aqueous acid, such as a dilute aqueous strong mineral acid, such as hydrochloric acid, sulfuric acid, phosphoric acid, or the like, or a dilute aqueous organic acid such as dilute aqueous acetic acid, at a temperature of about room temperature to about 50°C. for about 2–24 hours. The pH is about 1–4.

The compound (VI) may also be represented by its tautomer

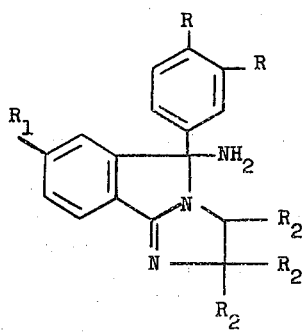

(VII)

where

R, $R_1$, $R_2$ and the provisos are as previously defined. Both tautomeric forms are within the scope of this invention and reference herein to one is intended to also be reference to the other. The particular tautomeric form present and the relative amounts of each will depend upon environmental factors such as pH and solvent.

These compounds (VI) and (VII) are new and novel and they represent an additional aspect of this invention. Moreover, the compounds form acid addition salts such as the mineral acid addition salts, e.g. the hydrobromide, hydrochloride, sulfate, phosphate, and the like, or organic acid salts such as the p-toluenesulfonate, acetate, benzoate and the like. These salts also represent an aspect of the invention.

In none of the above processes is the solvent, temperature or time of reaction critical in obtaining the indicated product. All these products are recovered by use of conventional techniques.

The dilithio derivatives of substituted 2-phenyl-2-imidazolines (III) are novel and represent an additional aspect of this invention. They are obtained by treating the corresponding unlithiated substituted-2-phenylimidazoline in inert atmosphere, e.g., nitrogen gas, and inert solvent, e.g. tetrahydrofuran, at a temperature of about 30°–100°C. for about 0.5–48 hours.

Some of the compounds of formulas (IV) and (V) and the substituted 2-phenyl-2-imidazolines are known and may be prepared according to methods disclosed in the literature. Those compounds of formulas (IV) and (V) and said imidazolines not specifically disclosed in the literature may be prepared using analogous methods and known starting materials.

A preferred aspect of this invention includes those novel compounds and processes wherein R and $R_1$ represent H and halo as defined above (R′ and $R_1′$).

EXAMPLE 1

7-Chloro-5-(p-chlorophenyl)-2,3-dihydro-5H-imidazo[2,1-a]isoindol-5-ol

A stirred solution of 17.0 g. (0.094 mole) of 2-(p-chlorophenyl)-2-imidazoline in 200 ml. of dry tetrahydrofuran blanketed under nitrogen gas is treated dropwise (15 minutes) with 200 ml. of 1.6 Molar n-butyllithium (0.28 mole) of butyllithium) in hexane. The mixture is heated at 50°C. for three hours to obtain the N,o-dilithio derivative of 2-(p-chlorophenyl)-2-imidazoline which is then treated with 38 g. (0.22 mole) of methyl-p-chlorobenzoate in 200 ml. of tetrahydrofuran.

After an additional five hours at 50°C., the mixture is cooled to 10°C. and treated dropwise with 54 ml. of saturated ammonium chloride solution. After stirring for two hours at room temperature, the resultant solid is filtered off and crystallized from dimethylformamide to give 7-chloro-5-(p-chlorophenyl)-2,3-dihydro-5H-imidazo[2,1-a]isoindol-5-ol.

When the above procedure is carried out and in place of 2-(p-chlorophenyl)-2-imidazoline, there is used equivalent amounts of a) 2-(p-fluorophenyl)-2-imidazoline,
b) 2-(p-tolyl)-2-imidazoline,
c) 2-(p-methoxyphenyl)-2-imidazoline, or
d) 2-(p-trifluoromethylphenyl)-2-imidazoline, there is obtained a) 7-fluoro-5-(p-chlorophenyl)-2,3-dihydro-5H-imidazo[2,1-a]isoindol-5-ol,
b) 7-methyl-5-(p-chlorophenyl)-2,3-dihydro-5H-imidazo[2,1-a]isoindol-5-ol,
c) 7-methoxy-5-(p-chlorophenyl)-2,3-dihydro-5H-imidazo[2,1-a]isoindol-5-ol, or
d) 7-trifluoromethyl-5-(p-chlorophenyl)-2,3-dihydro-5H-imidazo[2,1-a]isoindol-5-ol, respectively.

When the above-detailed process is carried out, in place of 2-(p-chlorophenyl)-2-imidazoline there is used e) 2-(p-chlorophenyl)-4-methyl-2-imidazoline, or
f) 2-(p-chlorophenyl)-4,4-dimethyl-2-imidazoline, there is obtained e) 7-chloro-5-(p-chlorophenyl)-2-methyl-2,3-dihydro-5H-imidazo[2,1-a]isoindol-5-ol, or
f) 7-chloro-5-(p-chlorophenyl)-2,2-dimethyl-2,3-dihydro-5H-imidazo[2,1-a]isoindol-5-ol, respectively.

EXAMPLE 2

7-Chloro-5-(p-fluorophenyl)-2,3-dihydro-5H-imidazo[2,1-a]isoindol-5-ol

A stirred solution of 17.0 g. (0.094 mole) of 2-(p-chlorophenyl)-2-imidazoline in 150 ml. dry tetrahydrofuran, blanketed under nitrogen gas is treated dropwise (15 minutes) with 200 ml. of 1.6 M. n-butyl lithium in hexane. The mixture is heated at 50°C. for three hours to obtain the N,o-dilithio derivative of 2-(p-chlorophenyl)-2-imidazoline which is then treated with 37 g. (0.22 mole) ethyl-p-fluorobenzoate in 300 ml. of dry tetrahydrofuran.

After an additional 5 hours at 50°C. the mixture is cooled to 10°C. and treated dropwise with 54 ml. of saturated ammonium chloride solution. After stirring for two hours at room temperature, the resultant solid is filtered off and crystallized from dimethylformamide to give 7-chloro-5-(p-fluorophenyl)-2,3-dihydro-5H-imidazo[2,1-a]isoindol-5-ol.

When the above detailed procedure is carried out and in place of ethyl-p-fluorobenzoate there is used a) 3-methyl benzoyl chloride,
b) methyl benzoate,
c) methyl p-methoxy benzoate,
d) methyl p-trifluoromethyl benzoate, or
e) methyl 3,4-methylenedioxy benzoate, there is obtained a) 7-chloro-5-(m-tolyl)-2,3-dihydro-5H-imidazo[2,1-a]isoindol-5-ol,
b) 7-chloro-5-phenyl-2,3-dihydro-5H-imidazo[2,1-a]isoindol-5-ol,
c) 7-chloro-5-(p-methoxyphenyl)-2,3-dihydro-5H-imidazo[2,1-a]isoindol-5-ol,
d) 7-chloro-5-(p-trifluoromethylphenyl)-2,3-dihydro-5H-imidazo[2,1-a]isoindol-5-ol, or
e) 7-chloro-5-(3,4-methylenedioxyphenyl)-2,3-dihydro-5H-imidazo[2,1-a]isoindol-5-ol, respectively.

EXAMPLE 3

5-(p-Chlorophenyl)-2-methyl-2,3-dihydro-5H-imidazo[2,1-a]isoindol-5-ol

To a flask equipped with a stirrer, condenser, and dropping funnel maintained under a nitrogen atmosphere, is charged 9 g. of 4-methyl-2-phenyl-2-imidazoline and 100 ml. of dry tetrahydrofuran. Over a 15 minute period and with stirring, 94 ml. of 1.6 M of n-butyllithium in hexane (0.15 moles of n-butyllithium) is added. The suspension is stirred for about 24 hours at room temperature to provide the N,o-dilithium derivative of 4-methyl-2-phenyl-2-imidazoline. A solution of 20.6 g. (0.15 mole) of 4-chlorobenzonitrile in 50 ml. of tetrahydrofuran is added and the mixture is refluxed for 2.5 hours, cooled in an ice bath and treated with 50 ml. of water. The organic layer is separated and concentrated in vacuo. The resultant residue which is a mixture of unreacted 4-chlorobenzonitrile, 4-methyl-2-phenylimidazoline and 5-amino-5-p-chlorophenyl-2-methyl-2,3-dihydro-5H-imidazo[2,1-a]isoindole is treated with 150 ml. of 10% aqueous hydrochloric acid at 50°C. for 16 hours. The resultant mixture is cooled in an ice bath with 2N sodium hydroxide until basic to litmus. The resultant solid is filtered off and crystallized from methanol-tetrahydrofuran (1:1) to give 5-(p-chlorophenyl)-2-methyl-2,3-dihydro-5H-imidazo[2,1-a]isoindol-5-ol. The above is the predominant product obtained, a lesser amount of 5-(p-chlorophenyl)-3-methyl-2,3-dihydro-5H-imidazo[2,1-a]isoindole also being obtained.

When the above process is carried out and 3,4-dichlorobenzonitrile or 3-fluorobenzonitrile is used in place of 4-chlorobenzonitrile, there is obtained 5-(3,4-dichlorophenyl)-2-methyl-2,3-dihydro-5H-imidazo[2,1-a]isoindol-5-ol or 5-(3-fluorophenyl)-2-methyl-2,3-dihydro-5H-imidazo[2,1-a]isoindol-5-ol, respectively.

When the above detailed process is carried out and in place of 4-methyl-2-phenyl-2-imidazoline there is used a) 4,4-dimethyl-2-phenyl-2-imidazoline,
b) 2-(p-chlorophenyl)-4-methyl-2-imidazoline, or
c) 4-methyl-2-(p-trifluoromethylphenyl)-2-imidazoline, there is obtained a) 5-(p-chlorophenyl)-2,2-dimethyl-2,3-dihydro-5H-imidazo[2,1-a]isoindol-5-ol,
b) 7-chloro-5-(p-chlorophenyl)-2-methyl-2,3-dihydro-5H-imidazo[2,1-a]isoindol-5-ol, or
c) 7-trifluoromethyl-5-(p-chlorophenyl)-2-methyl-2,3-dihydro-5H-imidazo[2,1-a]isoindol-5-ol, respectively.

As with the detailed procedure of this example hereinabove set out, the above method also provides in relatively minor amounts 3,3-dimethyl and 3-methyl isoindol-5-ols corresponding to those in a), b), and c) hereof.

What is claimed is:
1. A compound of the formula

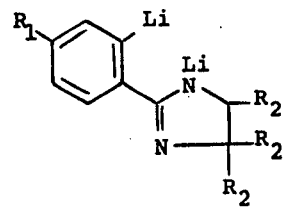

where
$R_1$ represents H, halo having an atomic weight of 19–36, lower alkyl, lower alkoxy or trifluoromethyl, and
each
$R_2$ independently represents H or alkyl having 1–2 carbon atoms,
provided that
1. when $R_1$ is H, at least one of $R_2$ represents other than H,
2. no more than two of $R_2$ are other than H, and
3. when two $R_2$'s are alkyl, they are the same.
2. A compound of the formula

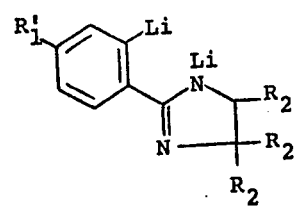

where
$R_1'$ represents H or halo having an atomic weight of 19–36, and
$R_2$ is as defined in claim 1,
provided that
1. when $R_1'$ is H, at least one of $R_2$ represents other than H,
2. no more than two of $R_2$ are other than H, and
3. when two $R_2$'s are alkyl, they are the same.

3. The compound of claim 2 which is N,o-dilithio-2-(p-chlorophenyl)-2-imidazoline.

4. The compound of claim 2 which is N,o-dilithio-4-methyl-2-phenyl-2-imidazoline.

* * * * *